(12) United States Patent
Ortmann

(10) Patent No.: US 8,489,203 B2
(45) Date of Patent: Jul. 16, 2013

(54) BIOSTABLE NEUROELECTRODE

(76) Inventor: Valerij Ortmann, Meckenheim (DE)

( * ) Notice: Subject to any disclaimer, the term of this patent is extended or adjusted under 35 U.S.C. 154(b) by 843 days.

(21) Appl. No.: 11/919,357

(22) PCT Filed: Apr. 26, 2006

(86) PCT No.: PCT/DE2006/000720
§ 371 (c)(1),
(2), (4) Date: Nov. 9, 2009

(87) PCT Pub. No.: WO2006/116968
PCT Pub. Date: Nov. 9, 2006

(65) Prior Publication Data
US 2011/0106229 A1 May 5, 2011

(30) Foreign Application Priority Data
Apr. 29, 2005 (DE) .......................... 10 2005 019 968

(51) Int. Cl.
*A61N 1/00* (2006.01)
*A61B 5/04* (2006.01)
(52) U.S. Cl.
USPC ............................ 607/116; 600/377; 600/378
(58) Field of Classification Search
USPC ............. 607/115–116, 53; 600/544, 377–378
See application file for complete search history.

(56) References Cited

U.S. PATENT DOCUMENTS

| | | | | |
|---|---|---|---|---|
| 5,215,088 A | * | 6/1993 | Normann et al. | 600/377 |
| 8,024,022 B2 | * | 9/2011 | Schulman et al. | 600/372 |
| 2002/0091421 A1 | | 7/2002 | Greenberg et al. | |
| 2003/0100823 A1 | * | 5/2003 | Kipke et al. | 600/378 |
| 2003/0176905 A1 | | 9/2003 | Nicolelis et al. | |
| 2004/0036485 A1 | * | 2/2004 | Sullivan | 324/694 |
| 2005/0277918 A1 | * | 12/2005 | Shah et al. | 606/41 |
| 2007/0197892 A1 | * | 8/2007 | Shen et al. | 600/378 |
| 2009/0248113 A1 | * | 10/2009 | Nimer et al. | 607/60 |

FOREIGN PATENT DOCUMENTS
EP    1 465 700 A2    10/2004

* cited by examiner

*Primary Examiner* — Christopher D Koharski
*Assistant Examiner* — Catherine Voorhees
(74) *Attorney, Agent, or Firm* — Pauley Petersen & Erickson

(57) ABSTRACT

A device for deriving electrical signals or for electrically simulating neuronal tissue. Neuroelectrodes form an interface between the biological tissue and technical systems. Existing neuroelectrodes for contacting low-lying neuronal layers diminish their properties by the interaction with biological tissue. In order to improve the long-time behavior, neuroelectrodes filled with bioactive substances are used. The neuroelectrode is formed on a flexible or rigid substrate with the aid of a line and of a microcapillary. The inside of the microcapillary serves as a container for the bioactive substance. The biostable neuroelectrode is used for deriving electrical signals or for electrically stimulating neuronal tissue in the fields of neurology and neurophysiology.

18 Claims, 8 Drawing Sheets

BIOSTABLE NEUROELECTRODE

BACKGROUND OF THE INVENTION

1. Field of the Invention

This invention relates to a device for electrical stimulation and signal derivation from neuronic tissue. More accurately stated, this invention relates to a multi-channel neuro-electrode for stimulating neurons in interior neuronic layers, or interior fibers of a nerve, which is suitable for extended time applications because of a particular stability.

2. Discussion of Related Art

During development of neuro-implants for correcting handicaps such as loss of hearing or blindness, a practical possibility for correcting further neurological handicaps, such as paraplegic handicaps, was recorded. While the first cochlear and retinal implants use sensory neurons in the sensory organs, such as the cochlea or retina, for transmitting information, in other applications the requirement exists for making a direct connection with neurons of different cortical regions. In most cases, these are located relatively deeply underneath the cortical surface and are difficult to access.

Two types of electrodes are known for making a connection with cortical neurons located a few millimeters beneath the surface: surface electrodes and penetrating electrodes. At present, cortical implants on the market have employed surface electrodes, which are placed over a target area and fastened. The main disadvantage of this solution is that very high currents are required for the stimulation of neurons in order to address the deeply located neurons.

A number of penetrating electrodes having several needle-like electrodes was developed as an alternative. An electrode array is described in U.S. Pat. No. 5,215,088, by which electrical pulses can be conducted out of interior cortical layers. The employment of these arrays as neuro-stimulators discloses some disadvantages of this solution: electrical losses in each electrode increase because of the use of doped silicon as the electrode material, because impedance can lie within the range of 300 to 800 KOhm. Therefore, energy consumption of the neuro-implant increases on the one hand and, on the other hand, the thermal stress on the nervous tissue in the vicinity of the electrodes increases. A further problem is posed by the manufacture of electrode profiles, such as shown in FIG. 1. Such a profile is required for the stimulation of different cortical layers which, for example, are responsible for various sensory representations of the image in the visual cortex.

A further embodiment of penetrating electrodes is described in US Patent Application 2003/0176905. Although this embodiment has excellent electrical properties, it is only suitable for acute employment, because it is not possible to construct the electrodes in a fully implementable manner because of the enormous size of the connecting elements. At the same time, the stiffness of the described electrodes is not sufficient for penetrating the nerves.

The stability over extended time causes another common problem of neuro-electrodes. Because of an interaction with biological tissue, a sort of a protective layer of neuroglial cells grows on the electrodes, which leads to a clear increase in stimulation thresholds and to the worsening of the signal quality. Investigations by Branner et al (2004) have shown that approximately 20% of the electrodes can no longer be used after 6 months in the body. Because the desired service life of neuro-implants is more than 10 years, this can result in the complete failure of the neuro-stimulator.

SUMMARY OF THE INVENTION

It is one the object of this invention to provide a penetrating neuro-electrode for the stimulation and signal derivation from the neuronic tissues, which assures the dependable and stable functioning of the neuro-implant over extended periods of time.

So that the electrical power loss in the electrodes can be kept as low as possible, metal conductors are used for connecting electrodes to the associated electronic components. The technical challenge with this is to connect the large number (100 to 1000) of required conductors with the electronic components, and is solved by a special method.

The connections are realized because the conductors become the basic element of neuro-electrodes, because of which the total volume of connecting points is minimized. This makes possible a space-saving construction of large electrode arrays with hundreds, or even thousands of electrodes.

The required mechanical stability of electrodes is achieved by using micro-capillaries. These are simultaneously used as electrical insulators for the electrical conductors.

So that the stability of neuro-electrodes is assured over extended periods, the interior of the micro-capillaries is filled with a bioactive substance, which prevents growth on electrodes. Filling also takes place by a special vacuum process.

BRIEF DESCRIPTION OF THE DRAWINGS

Certain embodiments of advantageous designs of neuro-electrodes and the associated methods will be represented in view of the drawings, wherein.

DETAILED DESCRIPTION OF THE INVENTION

Figure 1:
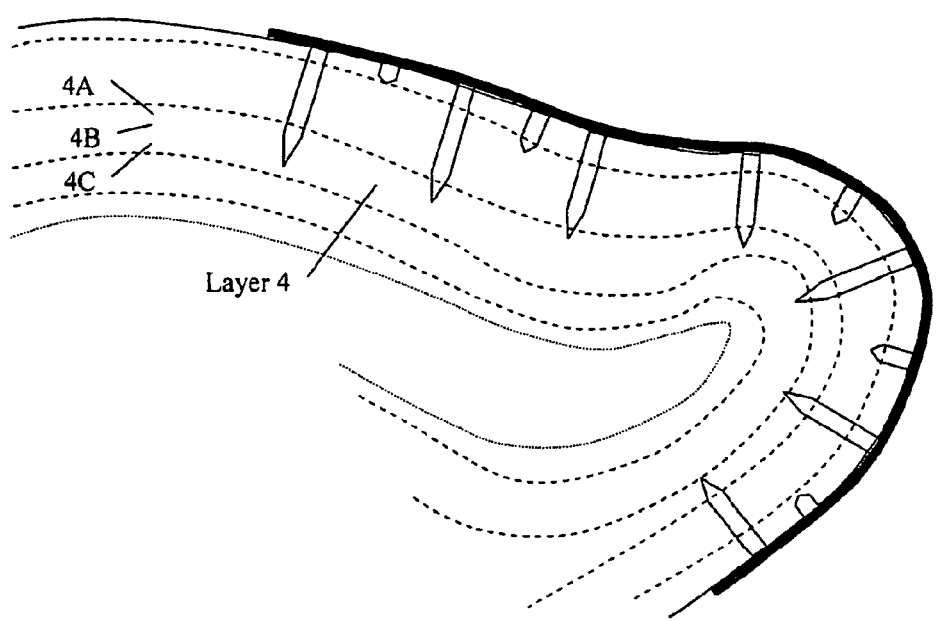
FIG. 1 shows a representation of an electrode array for stimulating different layers in the visual cortex of a human.

FIG. 1 represents a possible use of neuro-electrodes for the stimulation and derivation of signals in cortical layers of the brain. The structure of the visual cortex is schematically represented in several layers, with FIG. 1 showing the transition between the primary cortex V1 and the secondary cortex V2, and sublayers 4A, 4B, and 4C. It is known from neuro-physiological investigations that different layers of the cortex are responsible for different forms of representation of the information. For example, in the case of the visual cortex the information is conducted from so-called P and M receptor fields, which are responsible for contrast and movement, of the retina into the layer IV. But information regarding absolute brightness goes into the layer I. Since the layer I lies on the surface of the brain, and the layer IV at a depth of approximately 1 to 2 mm, it is required to have electrodes of different length in an electrode array. However, since the depth of the layer IV is irregular, the lengths of the electrodes should randomly deviate from the optimal length, so that at least a portion of the electrodes achieves the optimal placement in the layer IV.

Other cortical areas are also structured in accordance with the same multi-layer principle, and thus it is necessary to be able to vary the electrode lengths.

It is also possible to provide an exact matching of an electrode array with the patient because the surface structure of the brain is determined by a 3D scanner, and the structure of the layer structure with the aid of a functional test. The data obtained regarding the three-dimensional structure of the brain are used for matching the electrode lengths while producing the electrodes. In this way, the electrode array is exactly matched to the structure of the brain of the patient.

Figure 2:
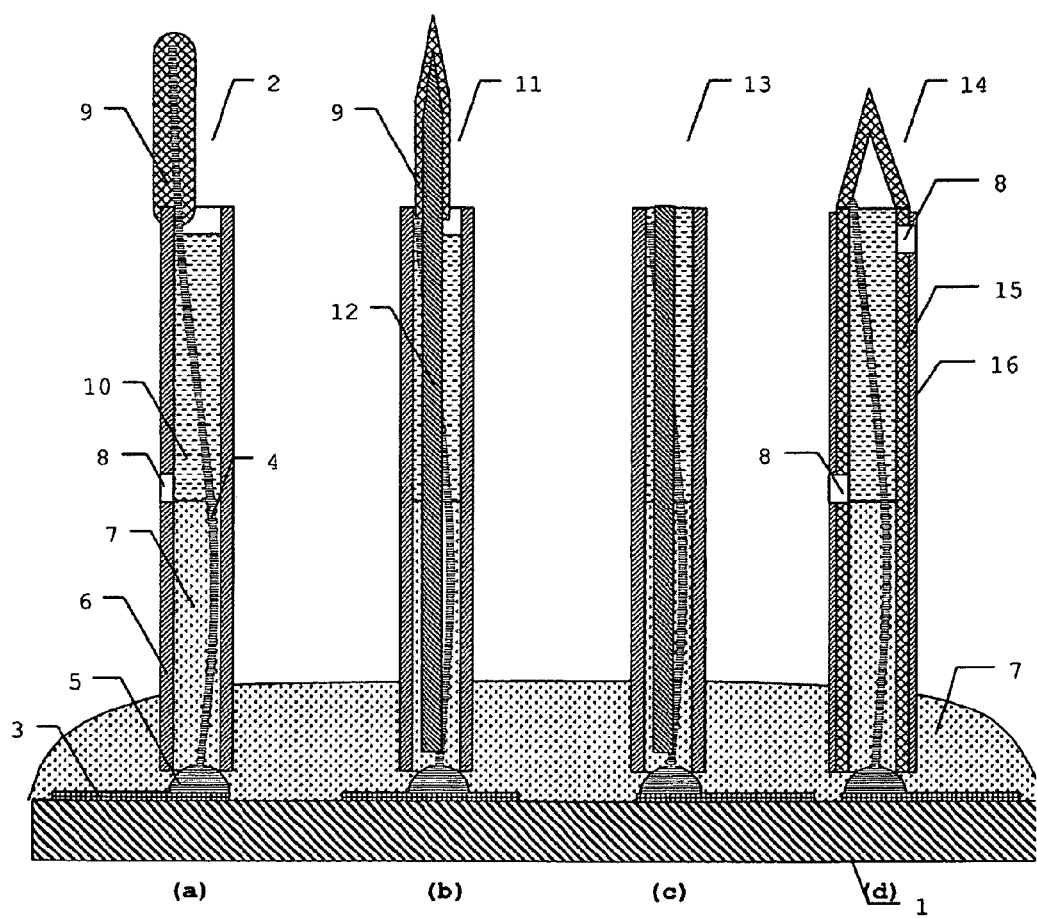
FIG. 2 shows embodiments of a biostable neuro-electrode.

FIG. 2a shows an advantageous embodiment of the electrode. An electrode 2 is built up on a substrate 1 and is connected with the electronic components by a strip conductor 3. Rigid, as well as flexible materials can be employed as the substrate 1. If the substrate 1 is flexible it is possible to match the entire electrode array flexibly to the surface of the brain or of a nerve.

Electronic printed circuit boards or semiconductors with integrated circuits represent a special type of substrates. In these cases, electrodes are for example constructed directly on the surface of the integrated circuit, so that additional connections between the electronic components and the electrodes are not necessary. The total size of the electrode array is thus clearly reduced.

A thin wire 4 made of gold, aluminum, platinum or other conductive materials constitutes the basis of the electrode 2. The wire 4 is connected with the strip conductor 3 by a welding, gluing or soldering process. The shape of the contact point 5 is a function of the connection method. A so-called thermo-compression ultrasound-ball-wedge bonding agent is employed in connection with the preferred embodiment, and thus the contact point 5 assumes an almost spherical shape. A micro-capillary 6 is stuck onto the wire 4. Depending on the application, it is possible to employ micro-capillaries made of various materials. Flexible electrodes are produced with the use of polymers such as PVC, PI, PTFE. These are sufficiently stiff for penetrating into the nerve tissue and are able at the same time to avoid harder types of tissue, such as blood vessels. This reduces damage to the blood vessels during implantation. If the tissue is covered with a further protective layer, rigid electrodes can be advantageous. In this case, micro-capillaries made of glass, ceramics, metals or other materials are used, which are of greater rigidity. The length of the micro-capillaries 6 is selected so that a portion of the wire 4 projects past or beyond the upper edge of the micro-capillaries 6. Later, this portion will constitute or form the electrode tip 9 to the neuronic tissue. The micro-capillary 6 is maintained on the wire 4 by means of an adhesive 7. The electrodes 2 are also maintained at a preset angle with respect to the surface of the substrate 1 by the same adhesive. Epoxy resin, silicone or other materials which, following application, change from the liquid state into an amorphous or hard state, can be employed as the adhesive 7. The liquid state during the application of the adhesive 7 is necessary if the interior of the capillaries 6 is intended to be sufficiently filled. The optimal filling of the electrode-2 is determined by the selection of the adhesive 7 and the processing, so that a portion of the electrode remains free for the bio-substance 10. A number of openings 8 is provided for better control of the gluing and make possible a simpler filling with the bio-substance 10. The open end of the wire 4 is coated with the electrode material prior to filling with the bioactive substance 10. Coating improves electro-chemical and mechanical properties of the electrode tips 9. The coating process is a function of the electrode material employed. In the preferred embodiment, such metals as platinum, iridium, palladium, steel alloys, gold or others are deposited by a galvanic process. Other coating methods, such as melting or sputtering, can be employed in the same way. Finally, following final processing, cleaning and sterilization, if required, the electrode 2 is filled with the bio-substance 10 in a bath.

For automating the electrode production, several micro-capillaries 6 made of plastic can be constructed on a common substrate by using a high-aspect rate structurization method, such as LIGA™ for example, and can thereafter be stuck together onto the wires 4.

So that the wires 4 are electrically insulated and have sufficient mechanical stiffness, it is possible to use a coating of epoxy resin, PI, PTFE, glass, p-xylylene or other suitable, non-conducting materials in place of micro-capillaries 6. The electrode tips 9 are freed of the insulating material by mechanical, chemical, thermal or electrical processing and, if required, they can be coated with further electrode material.

The use of the contact point 5 without the wire 4 represents a special type of electrode. Because of its spherical shape, the contact point 5 is very well suited for the stimulation of neurons on the surface of the nerve tissue. Simultaneously, the stimulation of different layers of the tissue is assured by a combination of penetrating and surface electrodes.

FIG. 2b represents a further advantageous embodiment of the electrode 11. Special alloys, such as PtIr for example, are often employed as the electrode material. Such alloys are widely used in neuro-physiology because of improved mechanical and electro-chemical properties. Since the deposition processes of such alloys often take place in a complicated and undependable manner, a further advantageous embodiment of the neuro-electrode is represented by using wire-like conductors 12 made of such alloys.

This is also employed if, because of the wear of the material during stimulation, a greater layer thickness of electrode material 9 is required. Many precious metals, such as Pt, Ir, Au or others can rarely be deposited at a layer thickness of more than 10 µm. In addition, it is possible to provide further coatings, or so-called activations of electrodes. When employing Pt or Ir, the surface is often "activated" in a further process step by an oxide formation, which makes possible an improved charge transfer during stimulation.

FIG. 2c shows a further advantageous embodiment of the electrode 13. In contrast to the previous explanations, it does not have a projecting end of the conductor 4. It is thus possible to perform the derivation of signals, as well as the stimulation, much more precisely in the local area around the electrode tip.

FIG. 2d shows a further advantageous embodiment of the electrode. The electrode 14 is formed by a metallic cannula 15 and, if required, has a non-conductive coating 16 of a polymer, such as PI, PTFE, PVC, p-xylylene or others.

Figure 3:
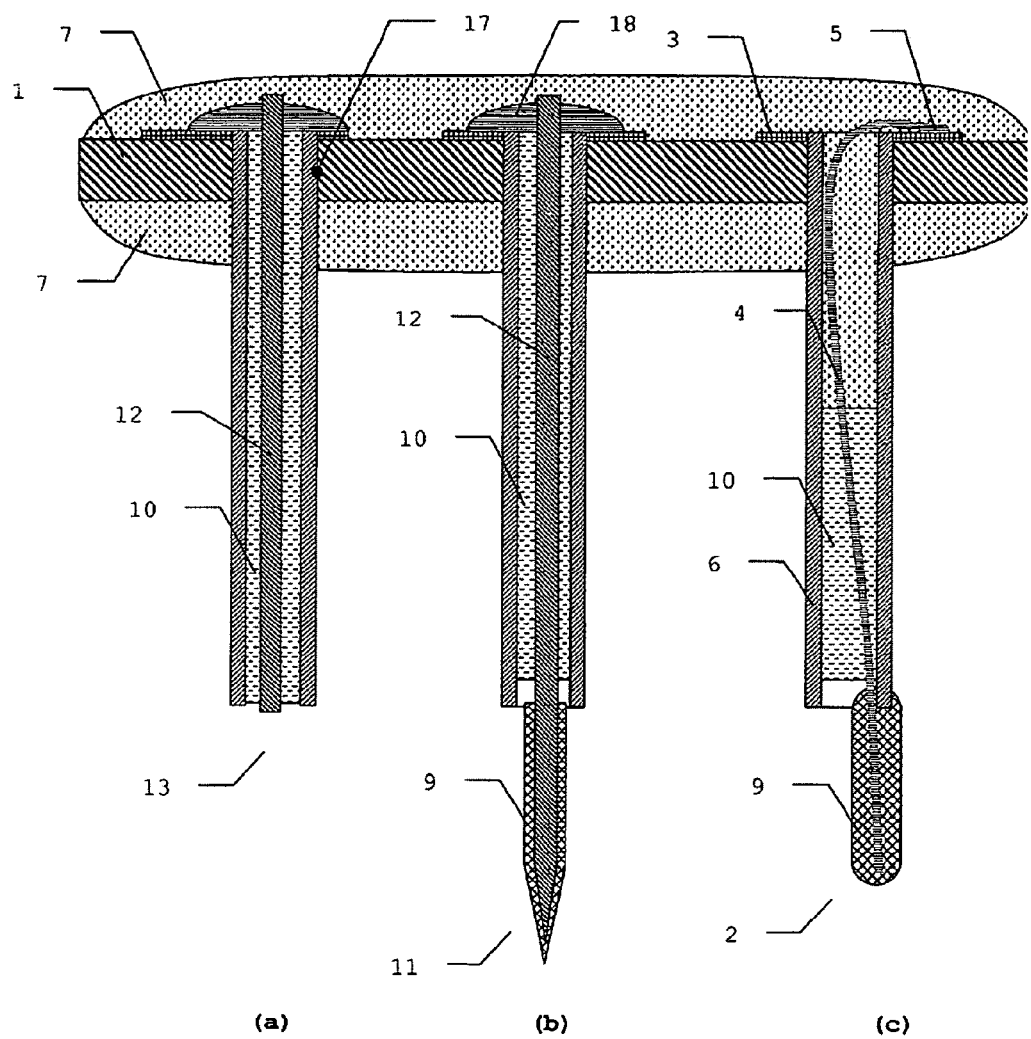
FIG. 3 shows further embodiments of a biostable neuro-electrode.

FIGS. 3a to c show further advantageous embodiments of the electrode. The substrate 1 has a number of openings 17 corresponding to the exterior diameter of micro-capillaries 6. Strip conductors 3, which are connected with the electrical components, are located at the edges of the openings 17. An electrical contact with the wire 4, 12 in the interior of the micro-capillaries 6 is established with the aid of a soldered, adhesive or welded connection 18, 5, for example wedge-wedge bonding agent.

Figure 4:
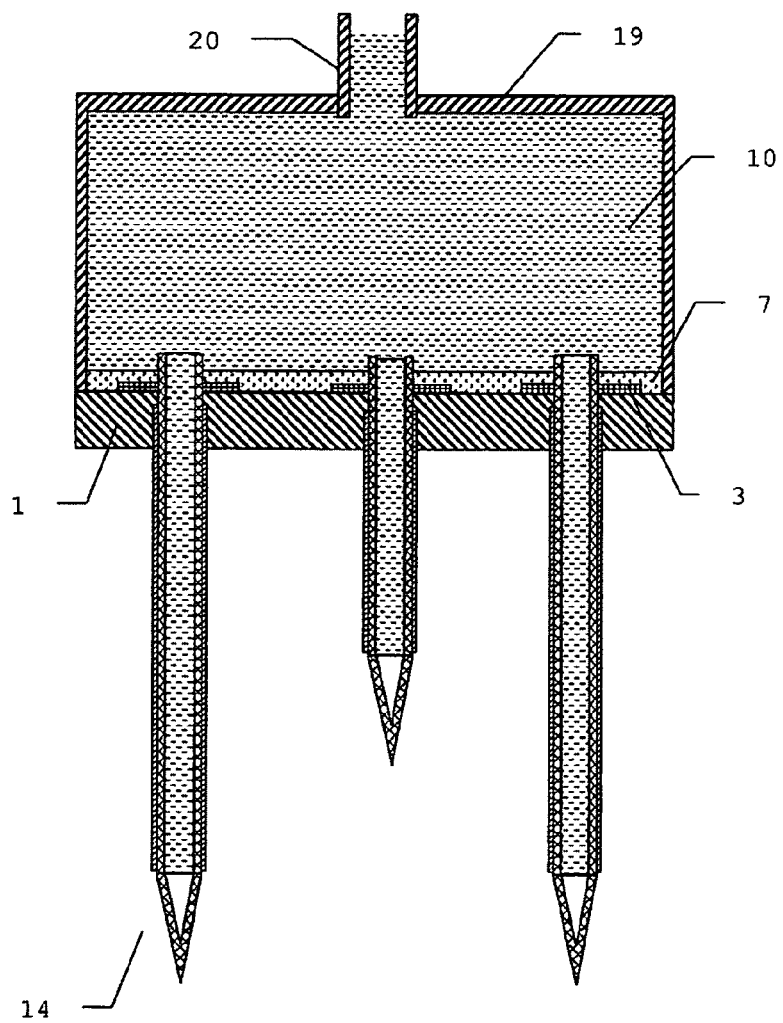
FIG. 4 shows still further embodiments of a biostable neuro-electrode.

FIG. 4 shows a further advantageous embodiment of the electrode. Because of the use of micro-capillaries a possibility exists of applying bioactive substances or cell cultures to the tissues simultaneously with electrical stimulation. A whole row of neuro-regenerative preparations employs a combination of various therapeutic agents for restoring neuronic tissues and for the functional restoration of the tissues. The electrodes 14 are constructed in a needle shape so that resistance is reduced during the introduction into the tissues. The container 19 for the cell cultures or the bioactive substances is fastened on the substrate 1. The contents of the container are applied to the tissues through the micro-capillaries 14 by a pump, or manually via the hose 20. This process can be externally controlled, wherein the depth of the application can be changed. Thus, the bioactive substance or the cell cultures are distributed through a larger volume of the tissues and it is stimulated to grow with the aid of electrical stimulation.

Figure 5:
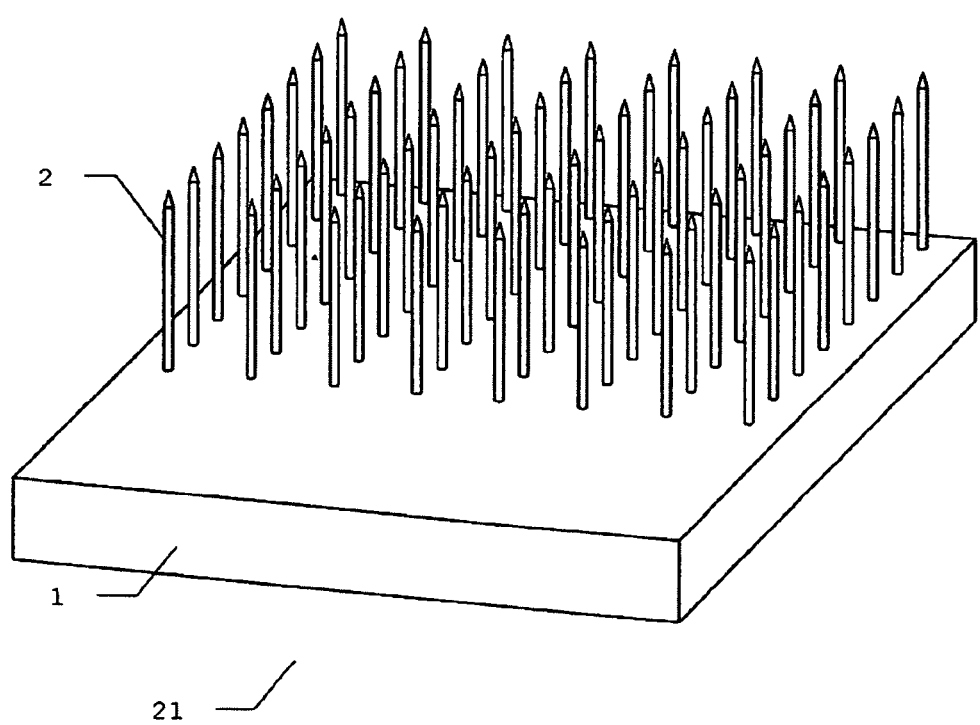
FIG. 5 shows a structure of an electrode array.
Figure 6:
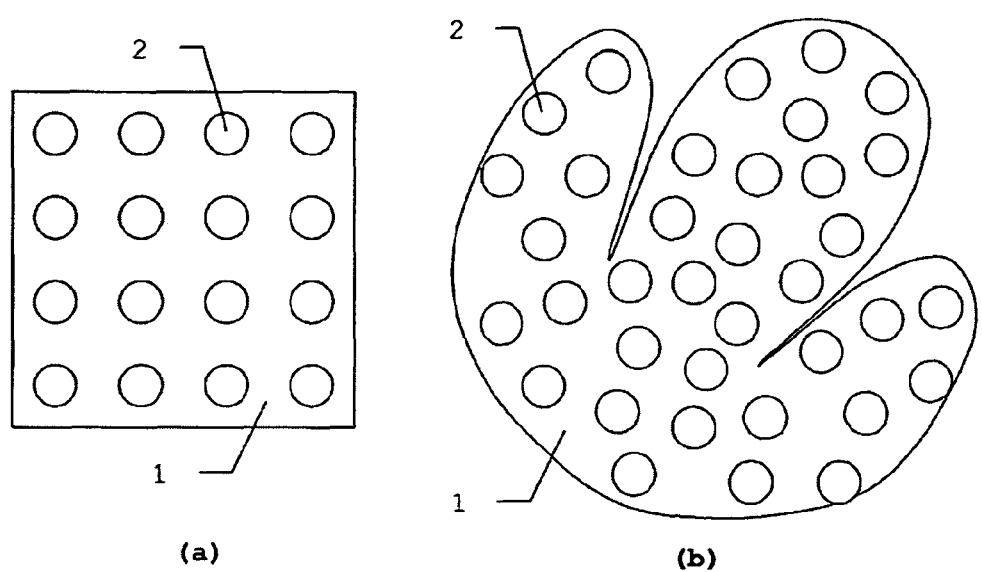
FIG. 6 shows an arrangement of electrodes on a substrate.

FIG. 5 shows a three-dimensional array 21 of several electrodes 2. The implantation of electrodes 2 takes place in groups of 10 to 100 electrodes fastened on a common substrate. The arrangement of electrodes 2, as shown in FIG. 6, on the substrate 1 can either be regular, as shown in FIG. 6a, or irregular, as shown in FIG. 6b, or can even be preset by an anatomical or physiological characteristic feature. For example, for optimizing local resolution in the visual cortex, the electrodes are placed in an irregular pattern, so that the actual resolution of the perception remains constant. With an approximately equal number of electrodes, the central areas clearly have a higher resolution than the periphery. This effect increases the consideration of the topographic image in the visual cortex and makes possible a significant reduction of the number of electrodes, along with the constant quality of the perception, or a clear improvement of the perception quality at a constant number of electrodes.

Figure 7:
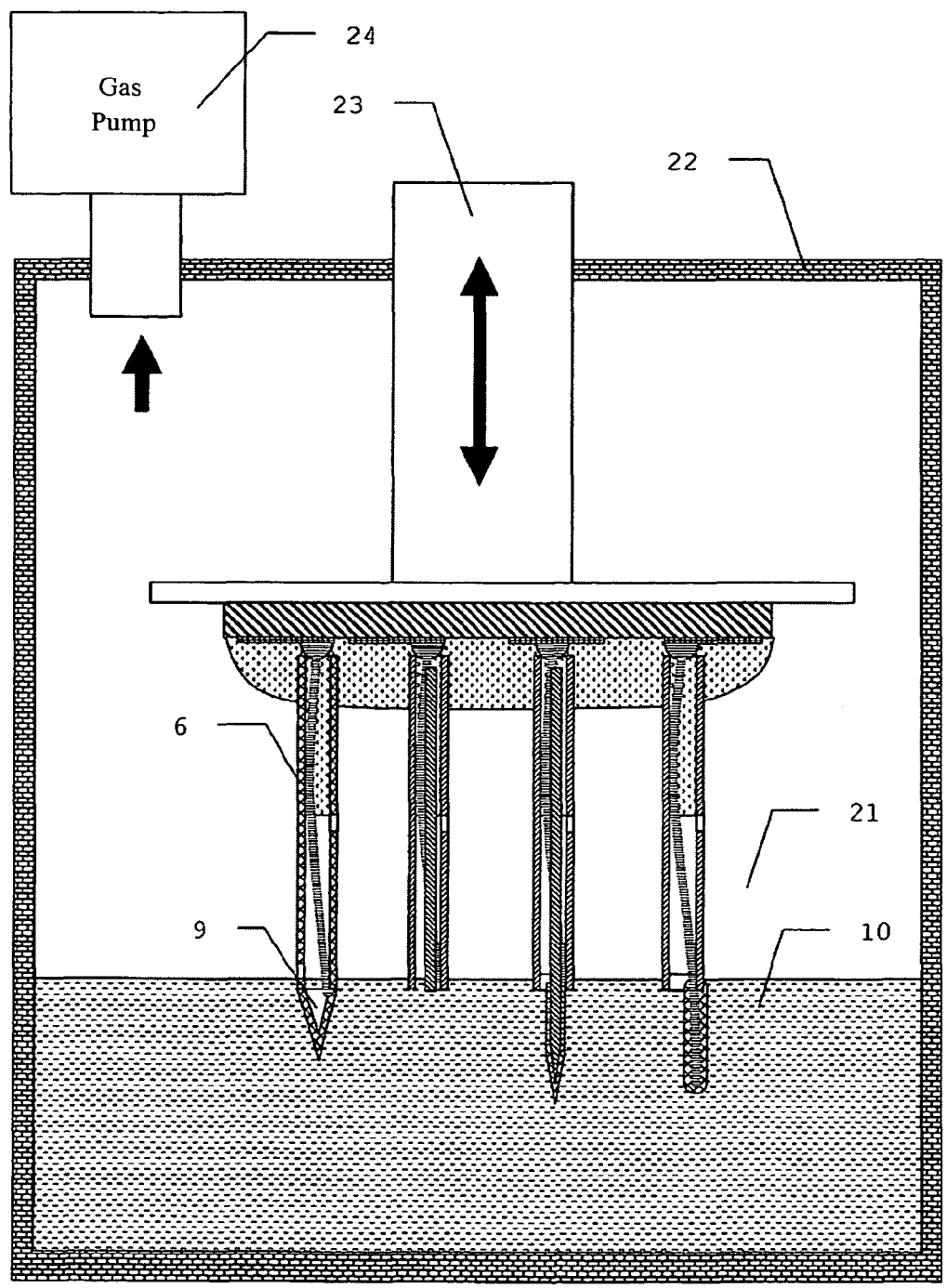
FIG. 7 shows a filling of micro-capillaries with the bioactive substance.

FIG. 7 represents a device 22 for filling electrodes with the bioactive substance 10. The electrode array 21 is fastened on a manipulator 23 in a gas-tight closed container 22. The container 22 is partially filled with the bioactive substance 10 in the liquid state. A gas pump 24 generates underpressure in the container 22. The underpressure should be selected so that the bio-substance 10 is not damaged. The electrode tips 9 of the electrode array 21 are dipped into the bio-substance, during which the liquid bio-substance fills the interior of the micro-capillaries 6 by capillary action. The array 21 is subsequently removed from the liquid and, following the restoration of normal pressure, it can be removed from the container 22, or packed up.

After the implantation into the tissues, the growth of neuroglial cells on the electrodes is clearly slowed, or even stopped, by the diffusion of the bioactive materials 10, such as neurotrophines or growth factors. It is possible to cause defined groups of neurons to grow specifically. The regeneration of the neuronic tissues is accelerated by a selective activation of growth factors in combination with electrical stimulation. The speed of diffusion is controlled by the size and number of openings 8 and by the bio-chemical properties of bio-substances.

Figure 8:
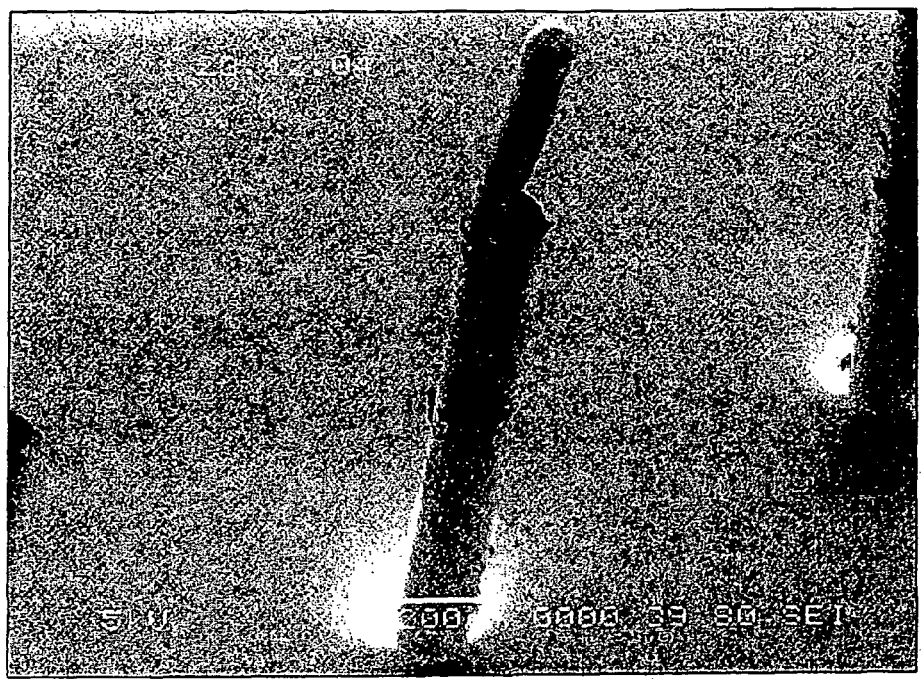
FIG. 8 shows realization of a neuro-electrode.

Investigations of test structures, as shown in FIG. 8, have shown that a fully automatic production of the described neuro-electrodes is possible by the employment of micromanipulators and automatic bonding agents. Mechanical tests in a tissue-like substance and animal testing experiments have shown both sufficient mechanical stability during implantation, as well as outstanding stability in the tissues over extended periods of several months.

The invention claimed is:

1. A device for a derivation of electrical signals and a stimulation of biological tissues, the device comprising:
a flexible and/or rigid substrate, the substrate including electrical strip conductors and at least one electrode extending substantially perpendicular from said substrate and connected with the electrical strip conductors, the at least one electrode having a micro-capillary with an interior and at least one opening, the micro-capillary being connected at one end with the substrate.

2. The device in accordance with claim 1, wherein the interior of the micro-capillary is filled with a neurotrophine or growth factor.

3. The device in accordance with claim 1, wherein the micro-capillary comprises at least one opening in the wall thereof.

4. The device in accordance with claim 1, wherein the electrode is fixed on the substrate by an adhesive or a casting resin.

5. The device in accordance with claim 1, wherein the electrode is fixed in an opening in the substrate.

6. The device in accordance with claim 1, wherein the electrode is fixed on the substrate by an epoxy, a resin, a silicone, a polyimide or a liquid glass.

7. The device in accordance with claim 1, further comprising an electrode array having electrodes of different length extending from the substrate.

8. The device in accordance with claim 1, wherein the micro-capillary is made of an electrically non-conductive material and an electrical conductor in a form of a wire is placed in the interior of the micro-capillary.

9. The device in accordance with claim 8, wherein the micro-capillary is made of a polymer selected from a polyimide (PI), a polytetrafluoroethylene (PTFE), a polyetheretherketone (PEEK), a polymethylmethacrylate (PMMA), a polyvinylchloride PVC, a silicon or a p-xylylene, or of a ceramic or a glass.

10. The device in accordance with claim 8, wherein an end of the wire projects beyond an edge of the micro-capillary 11. The device in accordance with claim 8, wherein an end of the wire has a conductive coating.

12. The device in accordance with claim 11, wherein the conductive coating is selected from gold, platinum, aluminum, copper, iridium, palladium, stainless steel, or alloys thereof, IrOx, platinum-black, platinum-gray, nanotube, or other fractal coating.

13. The device in accordance with claim 12, further comprising an electrode array, and electrodes in the electrode array arranged in an irregular pattern.

14. The device in accordance with claim 1, wherein the interior of the micro-capillary is filled with a biological or chemical substance.

15. The device in accordance with claim 14, wherein the substrate has a container for the biological or chemical substance.

16. The device in accordance with claim 1, wherein the micro-capillary of the electrode is made of an electrically conducting metal material.

17. The device according to claim 16 wherein the electrode is provided with a non-conductive coating of a polymer including a polyimide (PI), a polytetrafluoroethylene (PTFE), a polyvinylchloride (PVC) or a p-xylylene.

18. A device for a derivation of electrical signals and a stimulation of biological tissues, the device comprising:
a flexible substrate and/or a rigid substrate .made of an electrically conductive material or a non-conductive material, the substrate having electrical strip conductors and at least one electrode connected with the electrical strip conductors and fastened in an opening in the substrate by an epoxy resin, a silicone, a polyimide or a liquid glass, wherein each of the at least one electrode has an interior electrical conductor insulated by an electrically non-conductive material in a form of a micro-capillary, the micro-capillary having at least one opening and connected at one end with a substrate and an interior of the micro-capillary filled with a biological substance or a chemical substance.

* * * * *